United States Patent
Neto

(10) Patent No.: US 8,536,143 B2
(45) Date of Patent: Sep. 17, 2013

(54) COMPOSITIONS TO TREAT BACTERIAL AND INFLAMMATORY AFFECTIONS IN PET ANIMALS DOSAGE FORM AND METHOD TO TREAT PET ANIMALS

(75) Inventor: Dolivar Coraucci Neto, Sertaozinho (BR)

(73) Assignee: Ouro Fino Participacoes e Empreendimentos Ltda, Alto da Boa Vista (BR)

( * ) Notice: Subject to any disclaimer, the term of this patent is extended or adjusted under 35 U.S.C. 154(b) by 147 days.

(21) Appl. No.: 12/532,065

(22) PCT Filed: Mar. 24, 2008

(86) PCT No.: PCT/BR2008/000085
§ 371 (c)(1),
(2), (4) Date: Mar. 19, 2010

(87) PCT Pub. No.: WO2008/113149
PCT Pub. Date: Sep. 25, 2008

(65) Prior Publication Data
US 2010/0173858 A1    Jul. 8, 2010

(30) Foreign Application Priority Data
Mar. 22, 2007  (BR) ...................................... 0700969

(51) Int. Cl.
*A61K 31/70* (2006.01)
*A61K 9/28* (2006.01)

(52) U.S. Cl.
USPC ........................................... 514/29; 424/474

(58) Field of Classification Search
USPC .......................................................... 514/29
See application file for complete search history.

(56) References Cited

U.S. PATENT DOCUMENTS 6,068,859 A * 5/2000 Curatolo et al. .............. 424/490
2006/0058247 A1 3/2006 Hata et al.

FOREIGN PATENT DOCUMENTS

| EP | 1568369 | 8/2005 |
|---|---|---|
| WO | WO 03/061704 A2 | 7/2003 |
| WO | WO 2004/082719 | 9/2004 |
| WO | WO 2005/044254 | 5/2005 |
| WO | WO 2006/093784 | 9/2006 |

OTHER PUBLICATIONS

International Search Report issued in International Application No. PCT/BR2008/000085 filed on Mar. 24, 2008.

* cited by examiner

*Primary Examiner* — Elli Peselev
(74) *Attorney, Agent, or Firm* — Laurence P. Colton; Smith Risley Tempel Santos LLC

(57) ABSTRACT

Compositions comprising at least one bactericidal antibiotic from the group of macrolides and a non-steroid anti-inflammatory with selective inhibiting activity for cycloxygenase 2 (COX-2). The present invention also refers to a dosage form of said compositions, as well as a method to treat pet animals, particularly dogs and cats. Compositions of the present invention are particularly useful for administration to provide animals with dosages of about 1.0 to 50 mg of compound A/kg of body weight of the animal and about 0.05 to 5.0 mg of compound B/kg of body weight of the animal, being compound A preferably azithromycin and compound B, meloxicam.

26 Claims, 1 Drawing Sheet

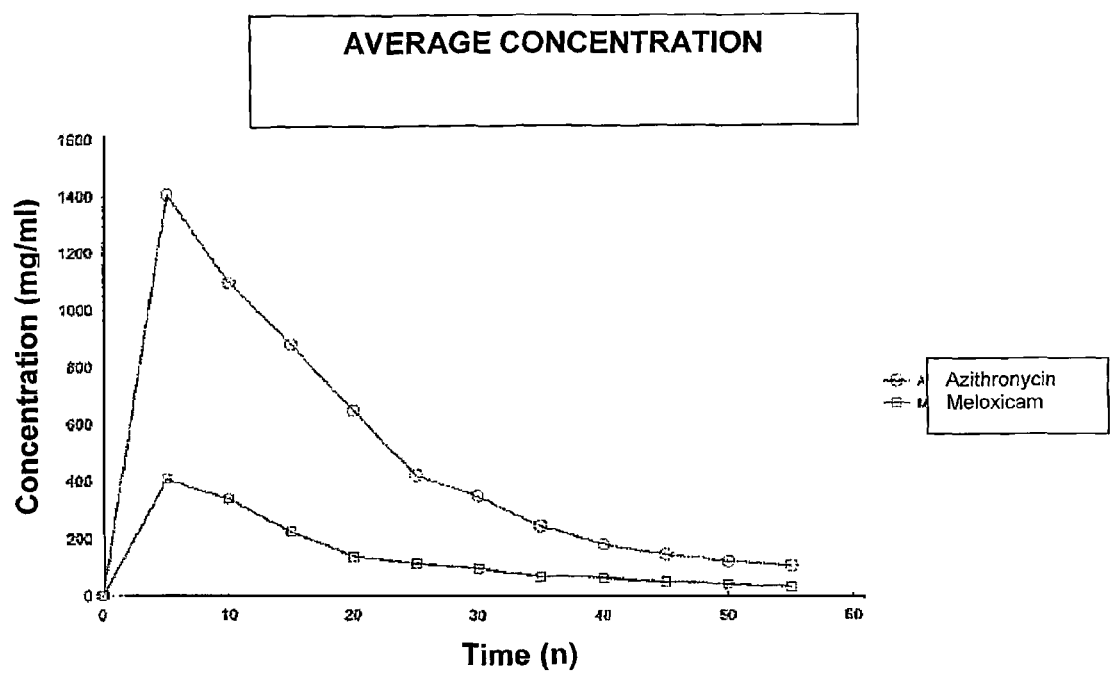

COMPOSITIONS TO TREAT BACTERIAL AND INFLAMMATORY AFFECTIONS IN PET ANIMALS DOSAGE FORM AND METHOD TO TREAT PET ANIMALS

STATEMENT OF RELATED APPLICATIONS

This application is the U.S. National Phase Under Chapter II of the Patent Cooperation Treaty (PCT) of PCT International Application No. PCT/BR2008/000085 having a filing date of 24 Mar. 2008, which claims priority on Brazilian Patent Application No. PI0700969-0 having a filing date of 22 Mar. 2007.

BACKGROUND OF THE INVENTION

1. Technical Field

The present invention refers to new compositions comprising at least one bactericidal antibiotic from the group of macrolides and a non-steroidal anti-inflammatory with selective inhibiting activity for cyclooxygenase 2 (COX-2).

The present invention also refers to dosage forms of said compositions, consisting of tablets and similar, provided with double coating layer.

Among the bacterial affections for which the compositions of the present invention are effective, we highlight respiratory affections caused by *Bordetella* spp, *Chlamydia* spp, *Haemophilus* spp, *Pasteurella* spp, *Shigella* spp, *Streptococcus* spp, *Escherichia coli*, *Staphylococcus aureus*; affections of the skin and attachments caused by *Corynebacterium* spp, *Staphylococcus aureus*, *Staphylococcus intermedius*, *Escherichia coli*, *Streptococcus* spp, *Pausterella multocida*; genitourinary affections caused by *Streptococcus* spp, *Escherichia coli*, *Staphylococcus aureus*); digestive affections such as diarrheas caused by *Escherichia coli*; oral affections such as gingivitis and periodontitis, as well as septic arthritis, osteomyelitis and discoespondilitis caused by *Escherichia coli*.

Compositions of the present invention are also indicated for use in post-surgery arthroplasties, bone surgeries, orthodontic surgeries, periodontal disease treatments or prophylaxis and general traumas in pet animals, particularly dogs and cats.

Among inflammatory affections for which the compositions of the present invention are effective, we highlight those disturbing the motor system, such as joints, bones and muscles, as well as other joints such as the spinal column. In this sense, the compositions of the present invention provide wide spectrum antibiotic therapy, combating the cause of infections, while treating inflammation and its effects.

Therefore, the present invention also contemplates a method to treat pet animals.

2. Related Art

Azithromycin is the first pharmaceutical product of the class of azalides. Azalides are derived from erythromycin and their mechanisms of action are similar. Azithromycin, or 9-deoxo-9a-aza-9a-methyl-9a-homoerithromycin A, has the molecular formula $C_{38}H_{72}N_2O_{12}$ and presents the following chemical structure:

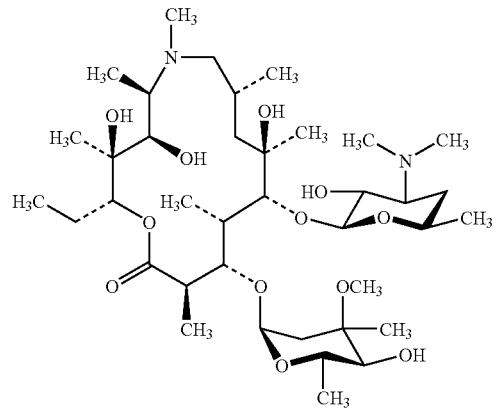

Technical and scientific literature about this pharmaceutical product is wide and discloses that azithromycin presents better oral absorption, is better tolerated, has much longer half-life, especially in tissues, and wide spectrum of activity. It is a modern antibiotic presenting, besides wide spectrum of action, pharmacokinetic characteristics allowing high intracellular concentrations and long permanence in tissues, thus providing therapeutic results with shorter treatment period. This antibiotic is active against Gram-positive aerobic bacteriae, *staphylococcus* and *streptococcus*, as well as anaerobic bacteriae. It has good activity against various intracellular microorganisms, including *Chlamydia* and *Toxoplasma*, being also active against mycobacteriae and *Mycoplasma*. Azithromycin is extraordinarily able to concentrate in tissues, particularly leucocytes, macrophages and fibroblasts. Concentration in tissues may reach up to 100 times the value of serum concentrations and concentrations in leucocytes may be of at least 200 to 300 times concentrations in serum. In cats, half life in serum is mentioned as being 35 hours, half life in tissues varies between 13 and 72 hours and $V_d$ is 23 l/kg. In dogs, azithromycin also presents quick absorption and persistent concentrations in tissues. $V_d$ is 12 l/kg, while half life in plasma and tissues is 29 to 90 hours, respectively. Oral absorption is high, with bioavailability values of about 58% in cats and about 97% in dogs. Therefore, it is particularly interesting that the intracellular reservoir of azithromycin may apparently produce efficient concentrations of the pharmaceutical product in gut fluids, even after plasma concentrations have fallen below detectable levels. Intracellular stocks of Azithromycin in leucocytes may also serve as a form to release the pharmaceutical product to infected tissues, especially in premature abscesses, since leucocytes are attracted to those places by chemotaxis. Slow release of Azithromycin by leucocytes distinguishes Azithromycin from other macrolides and fluoroquinolones which, despite reaching high concentration in leucocytes, are quickly released from cells in environments which are free from the pharmaceutical product.

Concerning anti-inflammatory products, the large majority available for veterinary use so far comprises active principles not selectively active for cyclooxygenase 2 (COX-2) and, despite having satisfactory analgesic and anti-inflammatory action, cause side effects in a large number of treated animals, mainly in cases requiring longer therapy. In these cases, due to the appearance of side effects, therapy should be interrupted before the resolution of the clinic profile. Among them, we can mention meloxicam, or 4-hydroxy-2-methyl-N-(5-methyl-2-thiazolyl)-2H-1,2-benzotiazine-3-carboxamide-1,1-dioxide, a compound with the molecular formula $C_{14}H_{13}N_3O_4S_2$ and structural formula:

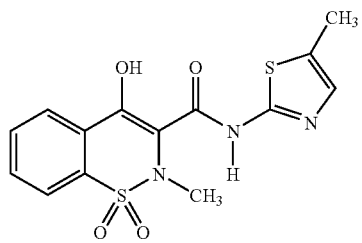 [SMILES: Cc1cnc(NC(=O)C2=C(O)c3ccccc3S(=O)(=O)N2C)s1]

Meloxicam is a powerful inhibitor of tromboxanes (TXs) and prostaglandins (PGs), with excellent antipyretic and analgesic properties, being used to treat affections of the muscles and skeleton, as well as pre-surgically. In the wide technical and scientific literature about such anti-inflammatory product, we found references considering it as a preferential COX-2 inhibitor. The main mechanism of action of meloxicam is to regulate the synthesis of prostaglandins, by inhibition of the enzyme system of cyclooxygenase (COX). Such action is responsible for the anti-inflammatory, anti-exudative, analgesic and antipyretic effects. Besides said effects, meloxicam also inhibits the infiltration of leucocytes into inflamed tissue and avoids bone and cartilage destruction as occurs in degenerative inflammation processes. In long term studies undertaken with rats and mice, meloxicam has shown chondroneutral action, being therefore especially indicated for long term treatments of osteoarthritis.

It is also known that the incidence of complications, such as hemorrhage and gastric perforation, is not equal for all non-steroidal anti-inflammatory products. There have been attempts to explain such differences based on "partial selectivity" for COX-2 inhibition. The existence of at least two isoforms of cyclooxygenase constituted by cyclooxygenase 1 (COX-1) and by COX-2 has recently been discovered. Isoenzyme COX-1 is responsible for the production of prostaglandins in the gastrointestinal route, promoting the protection of stomach mucosa against the action of gastric juice, and in kidneys, where they regulate its blood flow. The isoenzyme COX-2 has the main purpose to respond against inflammatory processes.

COX-2 selective inhibition causes an important reduction in the inflammatory process, without the consequences related to COX-1 physiological regulation feature. The clinical repercussion of said phenomenon is the inhibition of pain and inflammation with less toxicity in places where prostaglandins have an important action, such as in the stomach and kidneys. COX-2 is an inducible form, being formed from stimuli, such as the presence of endotoxins and inflammatory stimuli releasing cytokines which, on the other hand, induce the synthesis of COX-2 by cells such as macrophages, resulting in the release of inflammatory PGs, i.e. COX-2 is induced by the inflammatory reaction itself. The release of PGs together with proteases and other inflammatory mediators, such as oxygen-free radicals, result in inflammation.

Therefore, it has been hypothesized that COX-2 is the main responsible for the synthesis of prostanoid mediators of pain, inflammation and fever.

COX-2 route may be interrupted at various levels by antagonists or antibodies for cytokines and mitogens inhibiting COX-2 induction, such as glucocorticoids or effective COX-2 inhibitors. Therefore, the higher or lower probability of an AINE causing adverse effects is conditioned to its ability to selectively inhibit just COX-2. This knowledge made research turn to the discovery of drugs affecting COX-1 at a lower scale, thus having better safety margin and fewer side effects, keeping, on the other hand, enough actuation in COX-2 to provide a good analgesic, antipyretic and anti-inflammatory effect.

Studies made with meloxicam have shown that it acts selectively or preferentially at COX-2, promoting about 80 to 90% inhibition of said enzyme and about 20% only for COX-1 inhibition. This is why this is the elected drug for anti-inflammatory treatments, presenting excellent analgesic, antipyretic, anti-inflammatory and anti-exudative action with minimum side effects. Meloxicam is widely used for veterinary medicine as a general anti-inflammatory and particularly for pathological processes affecting bones, muscles and cartilages, where it acts by inhibiting the infiltration of defense cells into inflamed tissues. Experiments have proved the excellent actuation of that drug in muscle and skeleton affections which even need long anti-inflammatory therapy, being most indicated selective COX-2 inhibitors, such as meloxicam, due to the better safety margin, since dogs and cats are particularly affected by the side effects of anti-inflammatory therapies.

Pharmacokinetic studies made by giving meloxicam to rats, mice, dogs and guinea pig by oral and intravenous routes have shown that said compound has been well absorbed after oral administration in mice and dogs, with bioavailability of at least 70% in mice and 100% in dogs. Oral absorption is not changed by the simultaneous ingestion of food. Half life of the drug is between six and eight hours.

Various other experimental studies were carried out, both in Brazil and abroad, to prove the efficacy and tolerance of meloxicam in dogs and cats. One of them, conducted in Germany, evaluated the efficacy and tolerance of a treatment with meloxicam where animals have been submitted to twice and three times the recommended dosage of the active principle, administered by the subcutaneous parenteral route. No side effects or any hematological or chemical blood change have been observed. In a controlled field study, the clinical efficacy of meloxicam in dogs with acute motor disorders, when submitted to a one-week treatment with the drug, has been proved. During that week, side effect levels lower than 2% were noticed. The clinical efficacy was considered excellent or good in 87.9% and 95.3% of cases, respectively.

In another assay, conducted by the Octávio Bastos Veterinary Medicine Faculty—São João da Boa Vista, Sao Paulo, Brazil, meloxicam was administered to a group of dogs for twenty-one consecutive days, not causing any gastrointestinal dysfunction, change in mucosa color or animal appetite, showing higher tolerance to said drug for long treatments, in comparison with other anti-inflammatory products commonly used for dogs.

In another assay, conducted in Florida, United States, the clinical efficacy of meloxicam against ketoprofen in cats with painful motor disorders was evaluated. Sixty-nine dogs with acute or chronic motor disorders were recruited. Animals were treated for five consecutive days. Results have shown significant improvements in behavior, food ingestion and gain of weight and a significant reduction in claudicating, pain and inflammation. No differences between both treatment groups were noticed concerning measured parameters. Meloxicam was considered an effective analgesic product, well tolerated in cats with acute or chronic muscle and skeleton disorders in treatments of up to five consecutive days, also presenting a better palatability and easy administration for those animals.

In Madrid, an assay was carried out to evaluate the efficacy of meloxicam as an analgesic intended to control chronic pain, as well as its analgesic action when administered before surgical procedures. Obtained results have shown that meloxicam as administered before surgery presents large efficacy in surgical analgesia, significantly acting with opioids, reducing the required quantity of halothane to effect anesthesia and also providing an excellent rate of post-surgical analgesia due to its long period of action.

Furthermore, another assay conducted in Barcelona evaluated the efficacy and tolerance of meloxicam in dogs with change in the motor system. Results led to the conclusion that meloxicam is a powerful non-steroid anti-inflammatory with excellent clinical response in acute and chronic affections of the motor system. Tolerance against meloxicam was found in about 86.5% of cases. Secondary effects, as noticed during the three weeks of treatment, had less importance, since, except in one case, it was not necessary to suspend the medication.

The use of drugs Azithromycin and meloxicam is widely known in the therapy of dogs and cats. Azithromycin is a wide spectrum antibiotic. Meloxicam is a COX-2 selective non-steroidal anti-inflammatory product, thus reducing side effects, such as gastritis and reduction in immunity, being indicated for the treatment of general inflammatory processes. Frequently, meloxicam is prescribed for administration with antibiotics to minimize the inflammatory process generated in case of infections.

Currently, Azithromycin and meloxicam are administered separately; being the dog or cat forced to ingest at least one tablet of each substance, what makes the administration become difficult and may also cause worse stomach irritation. Furthermore, when two pharmaceutical products are administered in separate formulations, each substance will be absorbed at a time and the peaks of each pharmaceutical product will occur in different times. Thus, the effect of each pharmaceutical product is obtained in different times in the animal, and there is no simultaneous and complementary effect to the use of antibiotics and an anti-inflammatory product.

For the above reasons, Azithromycin and meloxicam have never been administered in one single dosage, for simultaneous treatments of bacterial and inflammatory affections.

BRIEF SUMMARY OF THE INVENTION

One of the objects of the present invention is, therefore, to provide new compositions comprising, as an active ingredient, an antibacterial agent and an anti-inflammatory agent.

Another object of the present invention is to provide a new tablet, tablet or similar comprising, as an active ingredient, an antibacterial agent and an anti-inflammatory agent, to be administered as a single dosage.

This and other objects are reached by the present invention by means of forms of dosage of said compositions, consisting in tablets and similar, provided with double coating layer.

BRIEF DESCRIPTION OF THE DRAWING FIGURES

FIG. 1 as attached shows bioavailability curves after the simultaneous administration, in one single dosage, of compound A and compound B, formulated as per the present invention. Curves show the average values of plasmatic concentration against time, obtained in experiments with twelve animals.

DETAILED DESCRIPTION OF PREFERRED EMBODIMENTS

The present invention has as its object, therefore, new compositions comprising at least one macrolide from the class of azalides (compound A) and a non-steroid anti-inflammatory compound B). Said compositions of the present invention are particularly useful for the treatment of bacterial and inflammatory affections attacking pet animals, particularly dogs and cats, providing antibiotic therapy with wide spectrum of action and combating the cause of infections, while treating inflammation and its effects.

Preferably, compound A of the present invention comprises azithromycin, erythromycin, clarithromycin, spiramycin, miocamycin or roxitromycin and compound B comprises meloxicam, tenoxicam, piroxicam, sudoxicam, isoxicam, ampiroxicam, droxicam, lomoxicam or cinoxicam.

Most preferably, compositions of the present invention comprise about 25% by weight of compound A, about 5% by weight of compound B and about 70% excipients, formulated in one single tablet, aiming to the sole administration of these both pharmaceutical products. Said tablet receives double coating, i.e. the active principle and the core are covered, so to allow both pharmaceutical products to be absorbed by the animal at the same time and under similar plasma peaks, thus providing, at the same time, double effective therapy.

Compositions of the present invention are intended to oral administration for pet animals, particularly dogs and cats, and comprise enough quantity to provide the animal with dosages of about 1.0 to 50 mg of compound A/kg of body weight of the animal and about 0.05 to 5.0 mg of compound B/kg of body weight of the animal. Preferably, compositions of the present invention will provide about 10 mg of compound A/kg of body weight of the animal and about 0.1 mg of compound B/kg of body weight of the animal.

More preferably, compound A is azithromycin and compound B is meloxicam.

For the purpose of the present invention, small-sized animals are those weighing 9 kg or less, medium-sized animals are those weighing between 9.5 kg and 23 kg, large-sized animals are those weighing between 23.5 kg and 40 kg, and giant-sized animals are those weighing more than 40.5 kg. This classification is not influenced by the race or age of the animal.

We include below examples of specific associations of Compound A with Compound B, active ingredients of the compositions of the present invention. These examples only suggest percentual rates of each active ingredient, compound A and compound B, not limiting nor restricting the scope of the present invention.

Example 1

For Small-Sized Dogs

Each tablet contains:

| | |
|---|---|
| Compound A | 50.0 mg (25%/200 mg core or 50%/100 mg core) |
| Compound B | 0.5 mg (0.25%/200 mg core or 0.50%/100 mg core) |

Example 2

For Medium-Sized Dogs

Each tablet contains:

| | |
|---|---|
| Compound A | 100.0 mg (25%/400 mg core or 50%/200 mg core) |
| Compound B | 1.0 mg (0.25%/400 mg core or 0.50%/200 mg core) |

Example 3

For Medium-Sized Dogs

Each tablet contains:

| | |
|---|---|
| Compound A | 200.0 mg (25%/800 mg core or 50%/400 mg core) |
| Compound B | 2.0 mg (0.25%/800 mg core or 0.50%/400 mg core) |

Example 4

For Large-Sized Dogs

Each tablet contains:

| | |
|---|---|
| Compound A | 300 mg (25%/1200 mg core or 50%/600 mg core) |
| Compound B | 3.0 mg (0.25%/1200 mg core or 0.50%/600 mg core) |

Example 5

For Large-Sized Dogs

Each tablet contains:

| | |
|---|---|
| Compound A | 400.0 mg (25%/1600 mg core or 50%/800 mg core) |
| Compound B | 4.0 mg (0.25%/1600 mg core or 0.50%/800 mg core) |

Example 6

For Giant-Sized Dogs

Each tablet contains:

| | |
|---|---|
| Compound A | 500.0 mg (25%/2000 mg core or 50%/1000 mg core) |
| Compound B | 5.0 mg (0.25%/2000 mg core or 0.50%/1000 mg core) |

In the above examples, the used quantity of active ingredient over the total weight of the tablet is about 25% of compound A and about 0.25% of compound B, always considering that the guaranteed therapeutic dosage is about 10 mg of compound A/kg of body weight of the animal and about 0.1 mg of compound B/kg of body weight of the animal.

Alternatively, the active ingredient compound A may be used in anhydrous or di-hydrated form.

The composition of the present invention should be orally administered during three to five consecutive days, and may be adjusted according to guidance from the veterinary physician.

Compositions of the present invention are formulated by using about 70% excipients. These excipients are one or more chosen from the groups as defined below:

Agglutinants/agglomerants/ligands—sucrose, glucose, lactose, starches, microcrystalline cellulose, Arabic and adraganth gums, gelatin, polyvinylpyrrolidone (PVP), pectin, alginic acid and alginates, hydroxypropylmethylcellulose, methylcellulose, ethylcellulose, sodium carboxymethylcellulose, paraffin, stearic acid, cocoa butter, polyethyleneglycols (PE), pre-gelatinized starch, sorbitol;

Disintegrants/disaggregants—starch, wheat starch ester, laminaria powder, pectin, agar-agar, casein, cellulose derivatives, microcrystalline cellulose, alginates, carbonates, bicarbonates, peroxides, glucose, lactose, carboxymethylamides, sodium glycolate starch, cellulose derivatives, sodium and calcium carboxymethylcellulose, crosslinked sodium carboxymethylcellulose, methylcellulose, purified cellulose, microcrystalline cellulose, alginic acid and alginates, bentonite, colloidal aluminum and magnesium silicate, gelatin, modified polyvinylpyrrolidone (crosslinked or crossed), pectin, formaldehyde-casein, cationic ion-changing resins, carboxyvinyl polymers, magmas, croscarmellose;

Diluents/filling material: USP lactose, anhydrous USP lactose, sucrose, directly compressible starches, hydrolyzed starches, mannitol, inositol, glucose, sorbitol, starches, partially hydrolyzed maize starch, microcrystalline cellulose, dibasic calcium phosphate, cocoa powder, kaolin, powdered milk, calcium carbonate, calcium sulphate, calcium phosphate, calcium citrate, magnesium oxide, magnesium carbonate, dextrin, talc, sodium chloride, kaolin, precipitated calcium carbonate, maltose, dextrose;

Absorbents/sorbents—wheat starch, rice starch, cassava starch, liquorice powder, dextrin, magnesium oxide, magnesium carbonate, tricalcium phosphate, kaolin, bentonite, colloidal silica, silicon dioxide;

Lubricants—talc, carboxyvinyl polymers, polyethyleneglycols, metal stearates, paraffins, various fats, surfactants, sodium laurylsulphate, sodium stearylfumarate, stearic and cetyl acid, stearic acid salts, mineral oil, colloidal silica, maize starch;

Sliders/flow promoters—talc, metal stearates, colloidal silica;

anti-adhesive—magnesium and calcium stearate, talc, silicon talc, starch, cellulose, silicone emulsion;

Non gastro-resistant coverings—hydroxypropylmethylcellulose, methylethyl hydroxycellulose, ethylcellulose, hydroxypropylcellulose, povidone, sodium carboxymethyl cellulose, polyethyleneglycols (PEG), acrylic acid polymers;

Enteric release coverings/gastro-resistant coverings—acrylic acid polymers and their derivatives, cellulose acetophthalate, hydroxypropylmethylcellulose phthalate (HPMCP) and its derivatives, polyvinyl acetophthalate (PVAP), alginates; Eudragit L100;

Plasticizers: triethylcitrate, polyethyleneglycols (PEG), cellulose acetophthalate, glycerin, castor oil, surfactants, propyleneglycol;

Coloring agents—pigments aluminum lakes FD&C or D&C such as aluminum lake Yellow 5—CI 19140, Yellow 6—CI 15985, Yellow 10—CI 47005, Blue 1—CI 42090, Blue 2—CI 70015, Brown—CI 20285, Red 2—CI 16185, Red 3—CI 45430, Red 6—CI 16255, Red 40—CI 16035, Green 3—CI 60730, Red 33—CI 17200, Violet 2—CI 60730, Blue 5—CI 42051, Red 4—CI 14700, Amaranth, Azorubine, Indigo Carmine, Sunset Yellow, Green Pear, Quinoline Yellow; iron oxide pigments; primary coloring agents FD&C or D&C such as Yellow 5 Tartrazine—CI 19140, Yellow 6 Sunset—CI 15985, Shining Blue 1—CI 42090, Blue 2 Indigotin—CI 70015, Blue 5 Patent—CI 42051, Red 2 Bordeaux—CI 16185, Red 3 Erythrosine—CI 45430, Red 5 Azorubine—CI 14720, Red 6 Ponceaux 4R—CI 16255, Red 40 Allura—CI 16035;

Flavoring/sweetening agents—natural and artificial sweetening agents;

Opacifier—titanium oxides, silicates (talc, aluminumsilicate), carbonates, sulphates, oxides and hydroxides;

Solubilizers—isopropyl alcohol, ethyl alcohol, mineral oil, ether, purified water, polyethyleneglycols (PEG).

Dosage forms as above disclosed, according to the present invention, introduce a new concept to the veterinary area, since it is a tablet with double cover, i.e. with covered active ingredient and core. Thus, compound A, due to its pharmacokinetics, should be absorbed by the gut, since low absorption occurs in acid or gastric media. Therefore, compound A receives a gastro-resistant film or covering. Compound B, on the other hand, is better absorbed in acid media and should be immediately released after its ingestion, for which reason it should be added to the core and have immediate release. After the final core compression, tablets receive a film, i.e. a cover for immediate release with the purpose to protect the tablet and improve its palatability.

Production process for the dosage form of the present invention involves two steps, i.e. two granulations, one to cover compound A and the other for the simple granulation of compound B, thus meeting pharmacokinetic requirements for the product.

Specific Formulations

In a typical but non-limitative embodiment of the present invention, a 200 mg tablet, tablet or similar has the following formulation:

| | |
|---|---|
| Azithromycin (di-hydrate) | 50 mg |
| Meloxicam | 0.5 mg |
| Purified water | 0.81 mg |
| Isopropyl alcohol | 150.2 mg |
| Microcrystalline cellulose PH 102 | 20 mg |
| Coloring agent Red Lake 40 | 0.291 mg |
| Silicon dioxide | 4 mg |
| Titanium dioxide | 1.744 mg |
| Magnesium stearate | 4.81 mg |
| Eudragit E100 | 6.1 mg |
| Eudragit L100 | 1.5 mg |
| Starch sodium glycolate | 4 mg |
| Lactose M 200 | 107.36 mg |
| PEG 400 | 0.75 mg |
| PEG 6000/Carbowax 6000 | 0.41 mg |
| Polyvinylpirrolidone K 30 | 5.89 mg |
| Sodium starch glycolate | 4 mg |
| Talc | 4.85 mg |

FIG. 1 as attached shows bioavailability curves after the simultaneous administration, in one single dosage, of compound A and compound B, formulated as per the present invention. Curves show the average values of plasmatic concentration against time, obtained in experiments with twelve animals.

What is claimed is:

1. A composition for treating bacterial and inflammatory conditions in a pet animal, wherein the composition comprises as active ingredients a macrolide antibacterial agent as a compound A and a non-steroidal anti-inflammatory agent as a compound B, wherein compound A is azithromycin and compound B is meloxicam, wherein the composition is formulated in a double covered tablet wherein compound A is covered by a gastro-resistant film or covering as one covering of the double covered tablet, compound B is added to compound A to form a core for the double covered tablet, and the core is covered by a non-gastro-resistant film or covering as another covering of the double covered tablet.

2. The composition of claim 1, further comprising about 25% by weight of compound A, about 5% by weight of compound B, and about 70% excipients, wherein the composition is formulated in the dosage form in one single double covered tablet.

3. The composition of claim 2, wherein the dosage form is administered to provide the pet animal with dosages of about 1.0 to 50 mg of compound A per kilogram of body weight of the pet animal and about 0.05 to 5.0 mg of compound B per kilogram of body weight of the pet animal.

4. The composition of claim 2, wherein the dosage form is administered to provide the pet animal with dosages of about 10 mg of compound A per kilogram of body weight of the animal and about 0.1 mg of compound B per kilogram of body weight of the animal.

5. The composition of claim 1, wherein the dosage form comprises, in one 200 mg tablet, the following components:

| | |
|---|---|
| Azithromycin (di-hydrate) | 50 mg |
| Meloxicam | 0.5 mg |
| Purified water | 0.81 mg |
| Isopropyl alcohol | 150.2 mg |
| Microcrystalline cellulose PH 102 | 20 mg |
| Coloring agent Red Lake 40 | 0.291 mg |
| Silicon dioxide | 4 mg |
| Titanium dioxide | 1.744 mg |
| Magnesium stearate | 4.81 mg |
| Eudragit E100 | 6.1 mg |
| Eudragit L100 | 1.5 mg |
| Starch sodium glycolate | 4 mg |
| Lactose M 200 | 107.36 mg |
| PEG 400 | 0.75 mg |
| PEG 6000/Carbowax 6000 | 0.41 mg |
| Polyvinylpirrolidone K 30 | 5.89 mg |
| Sodium starch glycolate | 4 mg |
| Talc | 4.85 mg. |

6. A method to treat a pet animal for bacterial and inflammatory conditions, comprising administering to the pet animal a composition comprising as active ingredients at least one macrolide antibacterial agent from the class of azalides as a compound A and a non-steroidal anti-inflammatory agent as a compound B in a dosage form comprising about 25% by weight of compound A, about 5% by weight of compound B, and about 70% excipients, formulated in one single double covered tablet, wherein compound A is covered by a gastro-resistant film or covering as one covering of the double covered tablet, compound B is added to compound A to form a core for the double covered tablet, and the core is covered by a non-gastro-resistant film or covering as another covering of the double covered tablet, and wherein compound A is azithromycin and compound B is meloxicam.

7. The method according to claim 6, wherein the pet animal is a dog or a cat.

8. The method of claim 6, wherein the dosage form is administered to provide the pet animal with dosages of about 1.0 to 50 mg of compound A per kilogram of body weight of the pet animal and about 0.05 to 5.0 mg of compound B per kilogram of body weight of the pet animal.

9. The method of claim 6, wherein the dosage form is administered to provide the pet animal with dosages of about 10 mg of compound A per kilogram of body weight of the animal and about 0.1 mg of compound B per kilogram of body weight of the animal.

10. A composition for treating bacterial and inflammatory condition in pet animals, the composition being formulated in one single double covered tablet, wherein the tablet comprises a core comprising:
about 25% by weight of azithromycin, which is covered by a gastro-resistant film or covering as one covering of the double covered tablet; and
about 0.25% of meloxicam, which is added to the core, wherein the core is covered by a non-gastro-resistant film or covering as another covering of the double covered tablet,
thereby allowing immediate release of the meloxicam after ingestion of the tablet by the pet animal and simultaneous bioavailability of both the azithromycin and the meloxicam to the pet animal body.

11. A method to treat a pet animal for bacterial and inflammatory conditions, comprising administering one single double covered tablet to the pet animal, wherein the tablet comprises a core comprising:
1.0 to 50 mg of azithromycin, which is covered by a gastro-resistant film or covering as one covering of the double covered tablet; and
about 0.05 to 5.0 mg of meloxicam, which is added to the core, wherein the core is covered by a non-gastro-resistant film or covering as another covering of the double covered tablet,
thereby allowing immediate release of the meloxicam after ingestion of the tablet by the pet animal and simultaneously bioavailability of both the azithromycin and the meloxicam to the pet animal body.

12. A method to treat a pet animal for bacterial and inflammatory conditions, comprising administering to the pet animal a double covered tablet comprising around 10 mg of azithromycin per kilogram of body weight of the pet animal and around 0.1 mg of meloxicam per kilogram of body weight of the pet animal, wherein the azithromycin is covered by a gastro-resistant film or covering as one covering of the double covered tablet, the meloxicam is added to the azithromycin to form a core for the double covered tablet, and the core is covered by a non-gastro-resistant film or covering as another covering of the double covered tablet.

13. The method, according to claim 12, wherein the pet animal is a dog or a cat.

14. A composition for treating bacterial and inflammatory conditions in a pet animal, wherein the composition comprises as active ingredients a macrolide antibacterial agent as a compound A and a non-steroidal anti-inflammatory agent as a compound B, wherein the composition is formulated in a dosage form in one single double covered tablet, wherein compound A is covered by a gastro-resistant film or covering as one covering of the double covered tablet, compound B is added to compound A to form a core for the double covered tablet, and the core is covered by a non-gastro-resistant film or covering as another covering of the double covered tablet.

15. The composition of claim 14, further comprising about 25% by weight of compound A, about 5% by weight of compound B, and about 70% excipients.

16. The composition of claim 14, wherein the dosage form is administered to provide the pet animal with dosages of about 1.0 to 50 mg of compound A per kilogram of body weight of the pet animal and about 0.05 to 5.0 mg of compound B per kilogram of body weight of the pet animal.

17. The composition of claim 14, wherein the dosage form is administered to provide the pet animal with dosages of about 10 mg of compound A per kilogram of body weight of the animal and about 0.1 mg of compound B per kilogram of body weight of the animal.

18. The composition of claim 14, 15, 16, or 17, wherein:
compound A is selected from the group consisting of azithromycin, erythromycin, clarithromycin, spiramycin, miocamycin, and roxitromycin; and
compound B is selected from the group consisting of meloxicam, tenoxicam, piroxicam, sudoxicam, isoxicam, ampiroxicam, droxicam, lomoxicam, and cinoxicam.

19. The composition of claim 18, wherein compound A is azithromycin and compound B is meloxicam.

20. A method to treat a pet animal for bacterial and inflammatory conditions, comprising administering to the pet animal a composition comprising as active ingredients at least one macrolide antibacterial agent from the class of azalides as a compound A and a non-steroidal anti-inflammatory agent as a compound B in a dosage form comprising about 25% by weight of compound A, about 5% by weight of compound B, and about 70% excipients, formulated in one single double covered tablet, wherein compound A is covered by a gastro-resistant film or covering as one covering of the double covered tablet, compound B is added to compound A to form a core for the double covered tablet, and the core is covered by a non-gastro-resistant film or covering as another covering of the double covered tablet.

21. The method of claim 20, wherein the dosage form is administered to provide the pet animal with dosages of about 1.0 to 50 mg of compound A per kilogram of body weight of the pet animal and about 0.05 to 5.0 mg of compound B per kilogram of body weight of the pet animal.

22. The method of claim 20, wherein the dosage form is administered to provide the pet animal with dosages of about 10 mg of compound A per kilogram of body weight of the animal and about 0.1 mg of compound B per kilogram of body weight of the animal.

23. The method of claim 20, 21, or 22, wherein:
compound A is selected from the group consisting of azithromycin, erythromycin, clarithromycin, spiramycin, miocamycin, and roxitromycin; and
compound B is selected from the group consisting of meloxicam, tenoxicam, piroxicam, sudoxicam, isoxicam, ampiroxicam, droxicam, lomoxicam, and cinoxicam.

24. The method of claim 23, wherein compound A is azithromycin and compound B is meloxicam.

25. A method to treat a pet animal for bacterial and inflammatory conditions, comprising administering to the pet animal around 10 mg of azithromycin per kilogram of body weight of the pet animal and around 0.1 mg of meloxicam per kilogram of body weight of the pet animal, wherein the azithromycin and the meloxicam is formulated in one single double covered tablet in which the azithromycin is covered by a gastro-resistant film or covering as one covering of the double covered tablet, the meloxicam is added to the azithromycin to form a core for the double covered tablet, and the core is covered by a non-gastro-resistant film or covering as another covering of the double covered tablet.

26. The method, according to claim 25, wherein the pet animal is a dog or a cat.

* * * * *